US009134332B2

(12) United States Patent
Frey et al.

(10) Patent No.: US 9,134,332 B2
(45) Date of Patent: Sep. 15, 2015

(54) INSTRUMENT AND PROCESS FOR THE AUTOMATED PROCESSING OF LIQUID SAMPLES

(75) Inventors: Rolf Frey, Ebikon (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/547,359

(22) Filed: Jul. 12, 2012

(65) Prior Publication Data
US 2013/0017535 A1    Jan. 17, 2013

(51) Int. Cl.
G01N 35/00        (2006.01)
G01N 35/10        (2006.01)
G01N 35/04        (2006.01)

(52) U.S. Cl.
CPC ............ G01N 35/0099 (2013.01); G01N 35/10 (2013.01); G01N 2035/00356 (2013.01); G01N 2035/00752 (2013.01); G01N 2035/0405 (2013.01); G01N 2035/0443 (2013.01); G01N 2035/0465 (2013.01); G01N 2035/0498 (2013.01); G01N 2035/103 (2013.01); Y10T 436/113332 (2015.01)

(58) Field of Classification Search
CPC .............. G01N 35/0099; G01N 35/10; G01N 2035/00356; G01N 2035/00752; G01N 2035/0405; G01N 2035/0443; G01N 2035/0465; G01N 2035/0498; G01N 2035/103; G01N 35/025; G01N 35/1002; G01N 35/04; G01N 35/00732; G01N 2035/1076; G01N 35/1065; G01N 2035/00346; G01N 2035/0463; G01N 35/00584; G01N 35/00722; B01L 2200/18; B01L 2300/021; B01L 3/02

USPC ................. 422/63, 65, 67, 64, 501; 436/180; 73/863.32, 864.24–864.25
See application file for complete search history.

(56) References Cited

U.S. PATENT DOCUMENTS

| 5,051,238 | A  | 9/1991 | Umetsu et al. |
|---|---|---|---|
| 5,639,425 | A  | 6/1997 | Komiyama et al. |
| 5,897,837 | A  | 4/1999 | Mizuno |
| 6,190,617 | B1 | 2/2001 | Clark et al. |
| 2002/0132356 | A1 | 9/2002 | Qureshi et al. |
| 2005/0123445 | A1 | 6/2005 | Blecka et al. |

(Continued)

FOREIGN PATENT DOCUMENTS

| EP | 0703455 B1 | 3/1996 |
|---|---|---|
| EP | 0745855 B1 | 12/1996 |
| EP | 1615037 A1 | 1/2006 |

*Primary Examiner* — Shogo Sasaki
(74) *Attorney, Agent, or Firm* — Roche Diagnostics Operations, Inc.

(57) ABSTRACT

An automated instrument and process for processing samples is presented. The instrument comprises a sampling area for receiving samples and reaction vessels; an analytical area with a first device resource comprising at least one analyzer; a reaction area comprising a conveyor for reagent containers; an incubator; a second device resource comprising first functional devices, the first functional devices having access to the sampling area and the incubator such as to transfer reaction vessels from the sampling area to the incubator and/or to pipette samples and/or reagents into the reaction vessels; a third device resource comprising second functional devices, the second functional devices having access to the incubator and the analytical area such as to transfer the reaction vessels from the incubator to the analytical area and/or to dispense liquids or withdraw liquids from the reaction vessels.

6 Claims, 10 Drawing Sheets

(56) References Cited

U.S. PATENT DOCUMENTS

| | | |
|---|---|---|
| 2007/0098597 A1 | 5/2007 | Brunner |
| 2008/0241939 A1 | 10/2008 | Matsuo et al. |
| 2008/0311678 A1 | 12/2008 | Ootani et al. |
| 2009/0117004 A1 | 5/2009 | Fritchie et al. |
| 2010/0236198 A1 | 9/2010 | Kraemer et al. |
| 2012/0301357 A1 | 11/2012 | Gut et al. |

INSTRUMENT AND PROCESS FOR THE AUTOMATED PROCESSING OF LIQUID SAMPLES

CROSS-REFERENCE TO RELATED APPLICATIONS

This application is a continuation of EP11173892.8, filed Jul. 13, 2011, which is hereby incorporated by reference.

BACKGROUND

The present disclosure generally relates to clinical analysis and medical diagnostics and, in particular, to an instrument and process for the automated processing of liquid samples.

In recent years, a strong demand for the automated analysis of liquid samples has been observed, which is primarily due to the fact that there is an ongoing increase in the number of clinical analyses. Sample analysis most typically involves mixing of the samples with one or more reagents for determining the absence/presence and optionally concentration of one or more analytes contained therein. Commercially available analyzers typically use pipetting robots for pipetting samples and reagents.

Many reagents have to be cooled and/or conditioned (e.g. mixed) before their use. In daily practice, it is convenient to cool-store the reagent containers obtained from a supplier and to leave the reagents therein until the reagent is needed. Commercially available instruments for the automated processing of liquid samples often comprise a dedicated loading device for loading the cooled reagent containers on a handling device such as a container carousel for withdrawing portions of the pre-cooled reagents contained therein with a pipette inserted through a container opening.

Due to the fact that reaction conditions may vary with temperatures, many reactions for analyzing liquid samples require that the sample/reagent mixtures are heated or incubated prior to transferring the reacted sample to an analyzer. Usually, the temperature of the sample/reagent mixtures is raised and kept constant for at least one specific time interval to enable the desired reactions to run and to provide a generally controlled environment under which the reactions may be carried out. As a result, comparable analytical results may be reliably obtained.

There is a need for an improved automated instrument for analyzing samples involving the use of cooled reagents to prepare sample/reagent mixtures and involving incubation of the sample/reagent mixtures in order to obtain the reacted sample that has a reduced footprint and has an improved workflow for processing the liquid samples.

SUMMARY

According to the present disclosure, an automated instrument for processing liquid samples is presented. The instrument can comprise a sampling area for receiving samples and reaction vessels, an analytical area comprising a first device resource comprising at least one analytical device for analyzing the samples, a reaction area comprising a conveyor provided with a plurality of holders for storing reagent containers for containing reagents and an incubator configured for receiving one or more of the reaction vessels for incubating the samples contained therein, and a second device resource comprising first functional devices selected from at least one first gripper for gripping the reaction vessels and at least one first pipettor for pipetting liquids. The first functional devices can have access to the sampling area and the reaction area such as to transfer reaction vessels from the sampling area to the incubator and to pipette samples and/or reagents into the reaction vessels. The instrument can further comprise a third device resource comprising second functional devices selected from at least one second gripper for gripping the reaction vessels and at least one second pipettor for pipetting liquids. The second functional devices can have access to the reaction area and the analytical area such as to transfer reaction vessels from the incubator to the analytical area and to dispense and/or withdraw one or more liquids to/from the reaction vessels transferred to analytical area. Finally, the instrument can comprise a controller, which operates the first, second and third device resources for processing a sample. At least two of the device resources can be at least temporarily operated in parallel for processing two or more samples.

In accordance with one embodiment of the present disclosure, a process for the automated processing of liquid samples is also presented. The process can comprise providing a conveyor having plural holders for storing reagent containers provided with one or more reagent containers. The holders are at least partly surrounding a central region containing an incubator for receiving one or more reaction vessels. A first gripper transfers at least one of the reaction vessels from a sampling area to the incubator. The conveyor can be moved with respect to the incubator such as to move at least one reagent container in a pipetting position for pipetting reagent contained therein. A first pipettor pipettes the reagent to the reaction vessel received in the incubator. The first pipettor pipettes sample contained in the sampling area to the reaction vessel in the incubator containing the reagent. The sample-reagent mixture can be incubated such as to obtain a reacted sample. A gripper can transfer the reaction vessel containing the reacted sample from the incubator to an analytical area provided with at least one analytical device for analyzing samples. The reacted sample can be transferred from the reaction vessel to the at least one analytical device for analysis thereof with respect to at least one analyte.

Accordingly, it is a feature of the embodiments of the present disclosure to provide an improved automated instrument for analyzing samples involving the use of cooled reagents to prepare sample/reagent mixtures and involving incubation of the sample/reagent mixtures in order to obtain the reacted sample that has a reduced footprint and has an improved workflow for processing the liquid samples. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure may be best understood when read in conjunction with the following drawings, where like structure is indicated with like reference numerals and in which.

DETAILED DESCRIPTION

Figure 1:
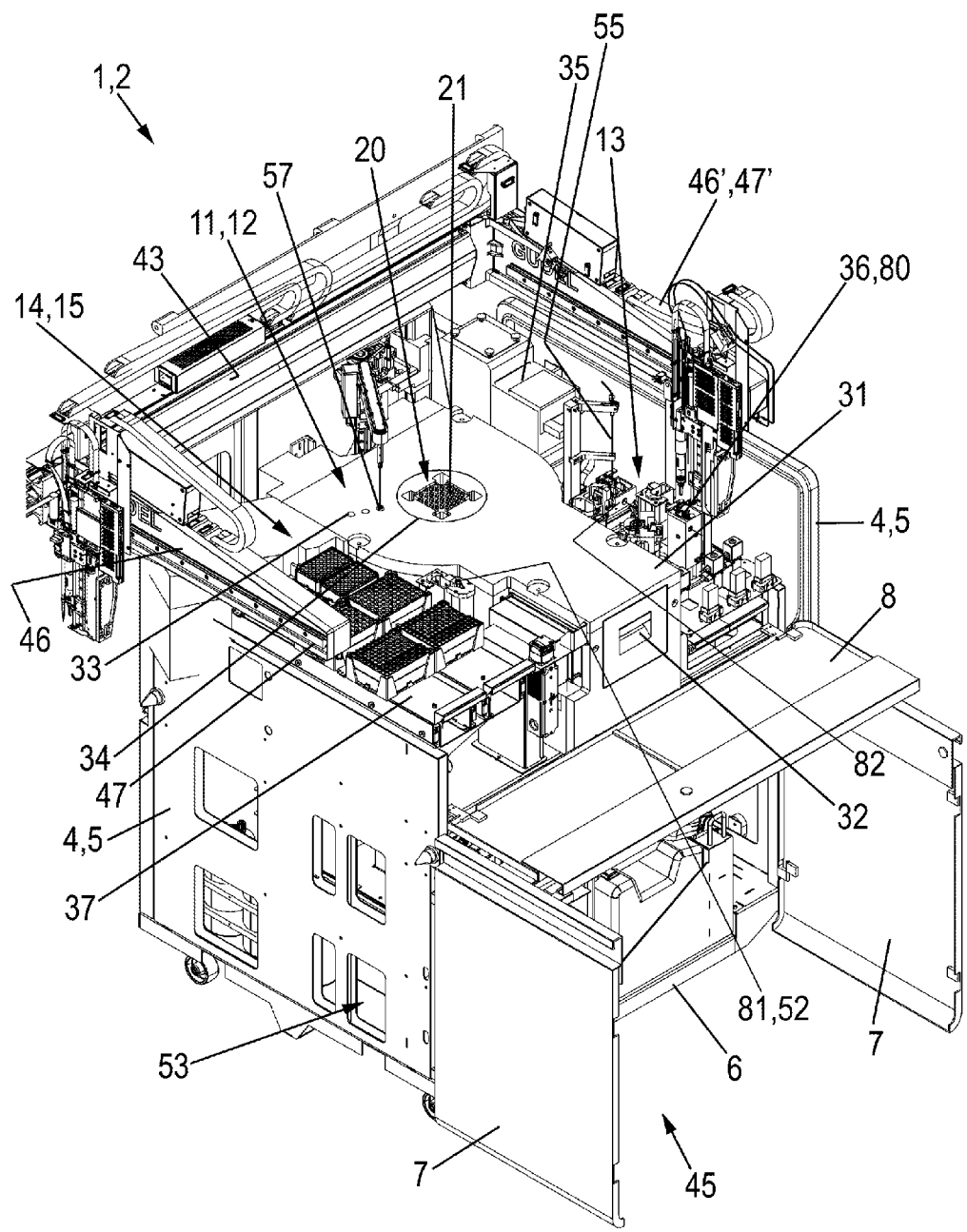
FIG. 1 is a perspective view of a first part of an exemplary instrument according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In this regard, terminology with respect to orientations and directions such as "horizontal", "vertical", "upper" and "lower" can be used with reference to the orientation of the figures being described. Because the components described can be positioned in a number of different orientations, this terminology is used for the purpose of illustration only and is in no way limiting.

An improved automated instrument for analyzing samples is herein presented, involving the use of cooled reagents to prepare sample/reagent mixtures and involving incubation of the sample/reagent mixtures in order to obtain the reacted sample. In particular, a size reduction of the instrument, especially with respect to the instrument's footprint is achieved. An improved workflow for processing the liquid samples is further presented.

The term "sample" generally relates to biological and non-biological (chemical) liquid fluids in which one or more analytes of interest can be present. Examples of biological fluids are body fluids like blood, serum, urine, saliva and cerebrospinal fluid. Biological fluids can, e.g., be subject to analyses and assays in medical and pharmaceutical research and clinical diagnosis, e.g., clinical-chemical or immunochemical analysis. Examples for non-biological fluids are samples of industrial waste water or environmental water drawn of lakes, rivers or springs. Non-biological fluids can, e.g., be subject to chemical analyses and assays, e.g., drug interaction screening, environmental analysis and identification of organic substances. Samples may also be pre-processed fluids such as extracts of body fluids, e.g., containing biological material in which nucleic acids may potentially be found. Samples may also be any other fluids or fluid extracts of interest such as, but not limited to, cells, tissues and microorganisms as long as an automated analysis thereof involves the use of one or more reagents. As used herein, the term "sample" may also relate to sample combined with one or more reagents.

As used herein, the term "reagent" generally relates to any liquid fluid suitable to be combined with liquid sample. In the more strict sense of the term, a reagent is a liquid solution containing a reactant such as a compound or agent capable of binding to or transforming one or more analytes present in a sample. Specifically, reactants can be mixed with the liquid sample so as to obtain a detectable change such as an optical signal emitted in response to one or more analytes contained therein. Reagents can also be mixed with any other reagent(s). Accordingly, reagents may contain reactants for reaction with one or more analytes contained in the sample. Examples of reactants are enzymes, enzyme substrates, conjugated dyes, protein-binding molecules, nucleic acid binding molecules, antibodies, chelating agents, promoters, inhibitors, epitopes, antigens and catalysts. Reagents, however, can also be non-reacting fluids such as buffers, solvents and diluting fluids.

As used herein, the term "reagent container" generally relates to reservoirs for containing liquids, each of which comprising a container body provided with a container opening to be opened or closed with a cap, such as, but not limited to, a hinged cap pivotably fixed to the container body or a removable cap that can be taken away from the container body. Examples for reagent containers are single reagent containers and reagent cassettes comprising plural reagent containers, e.g., serially arranged with respect to each other.

As used herein, the term "reaction vessel" generally relates to any vessel which can be used to react the sample with one or more reagents.

As used herein, the term "sample vessel" generally relates to any vessel which can be used to store a liquid sample.

According to a first aspect of the present disclosure, a new automated instrument for the processing of liquid samples is proposed. The instrument can, e.g., be adapted for the automated analysis of samples by performing tests or assays related to various immunochemical and/or clinical-chemical analysis items.

The instrument can comprise a sampling area for receiving the samples and reaction vessels. It can further comprise an analytical area provided with a device resource, in the following denoted as "first device resource", comprising at least one analytical device for analyzing the samples. As used herein, the term "resource" relates to one or more devices which can be used to process liquid samples.

The instrument yet further can comprise a reaction area which, e.g., can be arranged between the sampling and analytical areas, comprising a conveyor such as, but not limited to, a driven carousel provided with a plurality of holders for storing reagent containers for containing reagents and an incubator configured for receiving the reaction vessels for incubating samples contained therein. The sampling and analytical areas can, e.g., be located on different sides, e.g., on opposing sides, of the conveyor such as a carousel. As used herein, the term incubating relates to subjecting a sample to a predefined temperature or temperature profile for at least one predefined time interval.

The instrument of the present disclosure can yet further comprises another device resource, in the following denoted as "second device resource", comprising first functional devices selected from at least one first gripper for gripping the reaction vessels and at least one first pipettor for pipetting liquids such as samples and/or reagents. Specifically, the first functional devices can, e.g., be mounted to a driven first moving device. Furthermore, the first functional devices can have exclusive access to the sampling area and the reaction area, and not to have access to the analytical area, so as to transfer reaction vessels from the sampling area to the incubator and to pipette samples and/or reagents into the reaction vessels transferred to the incubator.

The instrument of the present disclosure can further comprises a yet another device resource, in the following denoted as "third device resource", comprising second functional devices selected from at least one second gripper for gripping the reaction vessels and at least one second pipettor for pipetting liquids such as reacted samples contained in the reaction vessels. Specifically, the second functional devices can, e.g., be mounted to a driven second moving device. Furthermore, the second moving device can have exclusive access to the reaction area and the analytical area, and not to have access to the storing area, so as to transfer reaction vessels from the incubator to the analytical area and to dispense and/or withdraw one or more liquids to/from the reaction vessels transferred to the analytical area.

The automated instrument further comprises a controller (electronic logic device) for controlling the analysis of liquid samples configured for operating the first to third device resources for processing a sample wherein at least two of the device resources are at least temporarily operated in parallel for processing two or more samples. More particularly, the controller can, e.g., be set up to operate one or more first functional devices of the second device resource, followed by operating one or more second functional devices of the third device resource and then followed by operating one or more analytical devices of the first device resource for processing a sample. The control can, e.g., be set up to successively (sequentially) operate the device resources in this order.

Furthermore, for processing two or more samples, the first to third device resources can be at least temporarily (partially) operated in parallel to process liquid samples in a highly time- and cost-effective manner. Moreover, the first functional devices can have exclusive access to the sampling area and the incubator and the second functional devices can have exclusive access to the incubator and the analytical area. Hence, the above-mentioned configuration of the first and second functional devices to selectively have access to the storing area and reaction area and the reaction and analytical area, respectively, can be reached by program-control. Furthermore, the controller can control operation of the first and second functional devices in a manner that the first and second functional devices have access to the incubator only one at a time, that is to say, the first functional devices or, alternatively, the second functional devices have access to the incubator.

In the above-described instrument, the controller can allow for program-control of the process of analyzing liquid samples, e.g., implemented in a dedicated hardware and/or software component, in the following denoted as "scheduler", configured to generate and assign time slots for operating the various devices resources for processing two or more liquid samples. Hence, the controller can control operation of the devices resources in a coordinated manner so as to avoid conflicts in processing liquid samples.

Due to the fact that the first to third device resources can at least temporarily be operated in parallel for processing two or more liquid samples, e.g., by moving and/or operating the first and second functional devices simultaneously in different areas of the instrument (the reaction area being a commonly accessible area), the instrument advantageously can allow a highly time- and cost-efficient analysis of several liquid samples at a time involving mixing of the samples with one or more reagents, incubating the sample/reagent(s)-mixtures to obtain reacted samples and analyzing the reacted samples by at least one analyzer.

According to one embodiment, the plurality of holders of the conveyor surrounds a central region at least in part, wherein the incubator is located in the central region. The conveyor can, e.g., be configured as driven carousel wherein the holders can be arranged in an annular row surrounding the central region. According to one embodiment, the incubator is kept stationary with respect to the reaction area so that the conveyor can be moved, e.g., rotated, with respect to the incubator. By arranging the incubator in the central region, the instrument can be made particularly small and compact in shape so as to allow for an improved workflow, e.g. by having small distances to transport vessels and liquids, for analyzing the liquid samples.

According to one embodiment, the instrument, e.g. the first moving device, can comprise a first transfer arm movable in a first direction and having at least one first transfer head movable in a second direction perpendicular to the first direction for mounting the one or more first functional devices. Furthermore, the instrument, e.g. the second moving device, can comprise a second transfer arm movable in the first direction and having at least one second transfer head movable in the second direction for mounting the one or more second functional devices. Hence, the first and second functional devices can be readily and quickly transferred to the various areas according to the control as implemented by the above-described scheduler. Furthermore, the instrument can be fabricated in a highly cost-efficient manner.

According to an embodiment, the instrument can comprise a cooling cell containing the conveyor such as a carousel for actively cooling the reagent containers stored by the holders, wherein the incubator is thermally isolated from the cooling cell. Hence, the instrument can advantageously allow for actively cooling the reagent containers without providing for a dedicated cool-storing compartment so as to reduce the size and foot-print of the instrument. Furthermore, due to the fact that the reagent containers can be used without necessity of transfer from a dedicated cool-storage to the conveyor, the workflow for analyzing the liquid samples can be improved. Furthermore, reagents can also be cooled during their use so as to avoid an increased degradation thereof and to improve the reliability of the analytical results. Moreover, by thermally insulating the incubator from the reagent containers stored on the conveyor, the reagents can be effectively cooled.

According to an embodiment, the conveyor such as a carousel can be operatively coupled to one or more of the following devices selected from:

1) a loader/unloader, arranged at the conveyor such as a carousel and for loading/unloading reagent containers to/from the holders. More particularly, the loader/unloader can be used to load/unload reagent containers to/from the conveyor, e.g., during analysis of the liquid samples so as to advantageously improve the workflow in sample processing.

2) an opener/closer, arranged at the conveyor and being adapted for opening/closing caps of the reagent containers stored by the conveyor. More particularly, the instrument can be configured for the use of reagent containers respectively comprising a cap that can be pivotably fixed with respect to a container body so as to be bi-directionally pivoted in an opening or closing direction. Specifically, the instrument can be configured to simultaneously open/close plural fluid containers, e.g., provided in a fixed arrangement such as a cassette. Accordingly, the instrument of the present disclosure can advantageously enable one or a plurality of fluid containers to be (e.g. simultaneously) opened and optionally closed. For instance, the opener/loader can be radially arranged with respect to the conveyor and can be provided with a carriage translatably movable towards and away from the carousel. Specifically, the carriage can, e.g., comprise a base portion and a pivoting portion pivotable with respect to the base portion so as to open and close, respectively, the reagent containers. Due to the fact that the carriage can be translated towards and away from the fluid containers to open/close the cap of each of the fluid containers by pivoting the pivoting portion thereof, the apparatus can advantageously be made small in vertical dimension thus leaving comparably large free space above the reagent containers enabling unhindered access to the reagent containers, e.g., with a pipettor or any other instrument used for manipulating liquids contained in the reagent containers such as, but not limited to, a liquid fluid mixer. In general, any device for manipulating the liquid fluids contained in the reagent containers can advantageously be arranged above the reagent containers.

3) a mixer, arranged at the conveyor and being adapted for mixing liquids contained in the reagent containers stored by the conveyor. More specifically, the mixer can, e.g., comprise a stirrer having a bar provided with a paddle which can be lowered into a reagent container for mixing liquid contained therein by rotating the stirrer around a longitudinal axis. As above-detailed, due to the radial arrangement of the opener/closer, the mixer can advantageously be arranged above the reagent containers so as to make the instrument small in its vertical dimension.

4) an identificator, capable of identifying the reagent containers stored by the conveyor.

According to an embodiment, one or more of the above-captioned devices are contained in the cooling cell. Hence, in the instrument, while manipulation of reagent containers and/or reagents contained therein is possible, the reagent containers can be cooled in a highly effective manner.

According to an embodiment, the sampling area is configured for storing disposable pipetting tips of the first pipettor. Hence, the instrument advantageously allows for the use of disposable pipetting tips to avoid sample carry-over which can readily be replaced after usage.

According to a second aspect of the present disclosure, a new process for the automated processing of liquid samples is proposed. According to an embodiment, the steps described below are performed successively (sequentially) to process liquid samples but they may also be performed in a different order. Specifically, the process can comprise a (e.g. first) step of providing a driven conveyor such as a rotatable carousel having plural holders for storing reagent containers provided with one or more reagent containers, wherein the holders at least partly surround a central region containing an incubator for receiving one or more reaction vessels. The holders can, e.g., be arranged in an annular row surrounding the central region.

The process can comprise a further (e.g. second) step of transferring at least one of the reaction vessels from a sampling area to the incubator using a first gripper.

The process can comprise a yet further (e.g. third) step of moving the conveyor (e.g. rotating the carousel) with respect to the incubator so as to move (e.g. rotate) at least one reagent container in a dedicated position, in the following denoted as "pipetting position", adapted for pipetting reagent contained therein.

The process can comprise a yet further (e.g. fourth) step of pipetting the reagent contained in the at least one reagent container to the reaction vessel received in the incubator using a first pipettor.

The process can comprises a yet further (e.g. fifth) step of pipetting a sample contained in the sampling area to the reaction vessel received in the incubator containing the reagent using the first pipettor so as to obtain a sample-reagent mixture.

The process can comprises a yet further (e.g. sixth) step of incubating the sample-reagent mixture so as to obtain a reacted sample.

The process can comprises a yet further (e.g. seventh) step of transferring the reaction vessel containing the reacted sample from the incubator to an analytical area having at least one analytical device for analyzing samples using a second gripper.

The process can comprise a yet further (e.g. eighth) step of transferring the reacted sample from the reaction vessel to the analytical device for analysis thereof with respect to at least one analyte.

Accordingly, the process of the present disclosure can advantageously allow for a reliable, highly time- and cost-efficient processing of liquid samples with respect to one or more analytes contained therein.

According to an embodiment, prior to incubating the sample-reagent mixture, the process can comprise a step of pipetting another reagent to the reaction vessel received in the incubator containing the sample-reagent mixture using the first pipettor. According to an embodiment, the further reagent can be taken from another reagent container already positioned in the pipetting position together with the first reagent container, e.g., as a reagent cassette comprising two or more reagent containers. According to an embodiment, this step can be combined with a step of moving the conveyor with respect to the incubator so as to move at least one further (other) reagent container in the pipetting position for pipetting reagent contained therein. This procedure can be performed once or several times according to the number of reagents to be added to the samples.

According to an embodiment, the process can comprise a step of opening and optionally closing the caps of one or more reagent containers prior to pipetting reagent contained therein. Accordingly, the reagent containers can be kept closed prior to their use and can optionally be closed after usage so as to avoid contamination and evaporation of reagents contained therein.

According to an embodiment, the one or more reagent containers stored by the conveyor can be actively cooled while being thermally isolated with respect to the incubator. Accordingly, the reagents can advantageously be cooled prior to, during and after their use in a highly effective manner.

According to an embodiment, one or more liquids can be dispensed to and/or withdrawn from the reacted sample contained in the reaction vessel using the second pipettor.

According to an embodiment, a second device resource comprising the first gripper and the first pipettor, a third device resource comprising the second gripper and the second pipettor and a first device resource comprising the analytical device can be sequentially operated for processing a sample wherein at least two of the device resources can be at least temporarily (partially) operated in parallel for processing two or more samples so as to improve the workflow in sample processing in order to perform sample analysis in a highly efficient manner. Specifically, at least one first functional device selected from the first gripper and the first pipettor can be simultaneously moved and/or simultaneously operated with at least one second functional device selected from the second gripper and the second pipettor.

According to an embodiment, the process can comprise one or more of the following steps:
  a step of opening a cap of at least one reagent container stored in the conveyor prior to pipetting reagent contained therein,
  a step of closing the cap of the reagent container stored in the conveyor after pipetting reagent,
  mixing reagent contained in the reagent container prior to pipetting reagent contained therein, identifying the reagent container stored by the conveyor prior to pipetting reagent.

The above-described various aspects and embodiments of the present disclosure may be used alone or in any combination thereof.

Figure 5:
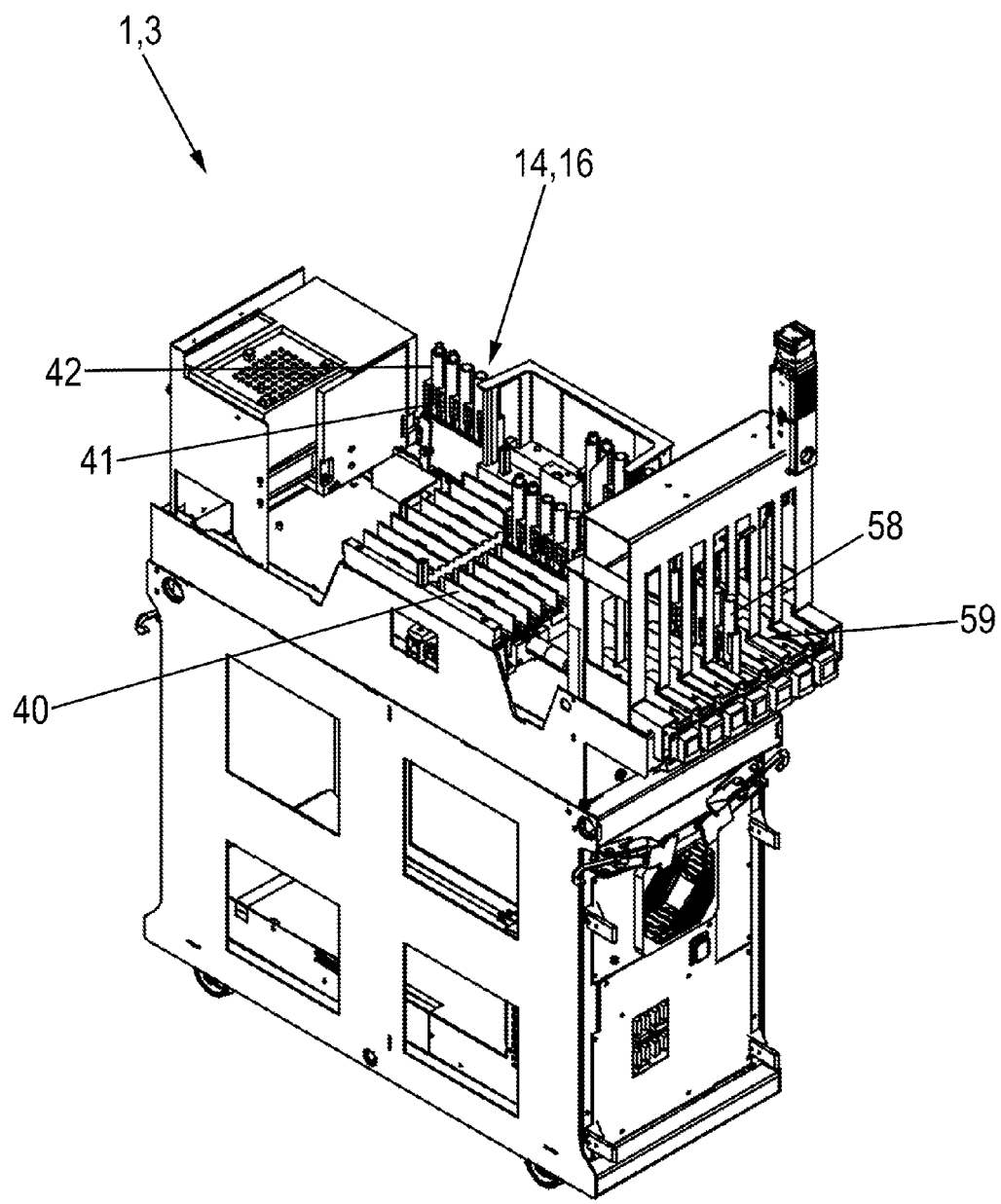
FIG. 5 is a perspective view of a second part of the exemplary instrument according to an embodiment of the present disclosure.

Initially, reference is made to FIGS. 1 and 5 illustrating a first part 2 and a second part 3 of an exemplary embodiment of the instrument for the automated processing of liquid samples generally referred to with reference numeral 1. The instrument 1 typically is provided with a top cover, which in the figures has been removed for the sake of clarity. The instrument 1 may be used in (bio-)chemistry including in-vitro diagnostics and can be adapted to carry out various assays comprising mixing of samples and reagents as well as detecting the result of those reactions. The instrument 1 can be used for analyzing liquid samples with respect to various immunochemical analysis items, e.g., using diagnostic assays such as immunoassays. It may be particularly useful for performing heterogeneous immunoassays wherein reactants such as capturing antibodies are immobilized on a solid support such as, but not limited to, magnetically responsive (i.e. magnetically attractable or magnetically repellable) particles. Such particles can, e.g., be embodied as magnetic beads or micro-spheres made of magnetically responsive material provided with immobilized reactants, e.g., molecular binding elements such as antibodies adapted to specifically bind to at least one analyte contained in the sample.

Accordingly, the instrument 1 comprises the first or right part 2 depicted in FIG. 1 and the second or left part 3 depicted in FIG. 5 as seen from the front-side of the instrument 1 indicated by the reference numeral 45. While the first and second parts 2, 3 are shown to be separated for the purpose of ease of illustration only, the two instrument parts are intended to be arranged side by side at the two mounting sides "A" to be secured to one another.

With particular reference to FIGS. 1 to 4, the first part 2 of the instrument 1 comprises a mount 4 provided with two side walls 5 and a base plate 6. At the front-side 45 of the instrument 1, two side doors 7 and a front cover 8 can be hinged to the mount 4 so as to grant access to the interior of the instrument 1 and to close the lower part of the instrument's front-side 45. The instrument 1 can be sectioned into several vertical levels, each of which comprising various components of the instrument 1 wherein the upper level 11 can be used as a processing or working zone for the analysis of liquid samples involving the transfer of reaction vessels and pipetting of fluids. In the following, only the upper level 11 of the instrument 1 is described in detail.

Accordingly, the working zone of the instrument 1 can be divided into several areas which can be structurally and/or functionally different entities (units). More particularly, the instrument 1 can comprise a reaction area 12 arranged between an analytical area 13 and a sampling area 14, the sampling area 14 being located on the one side (left side as seen from the front-side 45) of the reaction area 12 and the analytical area 13 being located on the other side (right side as seen from the front-side 45) of the reaction area 12. The sampling area 14 can comprise two sub-areas, i.e., a disposables storing area 15 provided by the first part 2 of the instrument 1 and a sample receiving area 16 provided by the second part 3 of the instrument 1 to be put in juxtaposition to the first part 2 at the left side wall 5 as above-described.

Specifically, the reaction area 12 can comprise a motor-driven rotatable carousel 17 having a plurality of holders 18 for storing reagent cassettes 19 which can be circumferentially arranged with respect to each other surrounding a non-rotatable (stationary) central region 20 of the carousel 17. Hence, the holders 18 and reagent cassettes 19 stored thereon, respectively, can be rotated around the central region 20 that is stationary with respect to the instrument 1. While the carousel 17 is shown with a number of 28 holders 18, those of skill in the art will appreciate that any other number of holders 18 can be envisaged according to the specific demands of the user.

An incubator 21 is located in the central region 20 of the carousel 17 having a plurality of receptacles 9 for receiving reaction vessels 60. Analysis of samples typically requires the samples to be combined with one or more reagents to initiate chemical or immunochemical reactions with respect to specific substances contained therein. Specifically, analytes contained in the samples can be bound to magnetically responsive particles provided with molecular binding elements that selectively bind to the analytes. Furthermore, the reaction vessels 60 can be used for labelling the particle-bound analytes with detectable labels such as fluorescence markers. The incubator 21 can be configured for incubating the sample/reagent mixtures contained in the reaction vessels 60, that is to say, to keep the temperature constant for predetermined time intervals so as to improve the reaction rates and to assure that reactions can be carried out in a generally controlled environment. The incubator 21 can, e.g., be configured to keep the temperature of the sample/reagent(s)-mixtures at about 37° C. (±0.3° C.).

The reaction area 12 further can comprise a loader/unloader 10 capable of loading/unloading reagent cassettes 19 to/from the holders 18 of the carousel 17. As can, e.g., be taken from FIG. 3, the loader/unloader 10 can comprise two transport lines 22 which at least in part can be in parallel alignment with respect to each other and are radially aligned with respect to the carousel 17. More particularly, the transport lines 22 can commonly be brought in juxtaposition to two adjacent holders 18 so as to establish a transport connection between the transport lines 22 and the holders 18. By rotating the carousel 17, two adjacent holders 18 can selectively be brought in juxtaposition to the transport lines 22 to load/unload the holders 18 of the carousel 17. Hence, reagent cassettes 19 can be bi-directionally transported to/from holders 18 according to the specific demands of the user, e.g., for charging the carousel 17 with reagent cassettes 19 and replacing empty reagent cassettes 19. Furthermore, the reagent cassettes 19 can be manually or automatically placed on or removed from the transport lines 22, e.g. with a robotic arm provided with a gripper for gripping the reagent cassettes 19.

The transport of the reagent cassettes 19 on the transport lines 22 can, e.g., be effected e.g. by a movable (driven) gripping pin (not illustrated) configured to be brought in gripping engagement with one or both reagent cassettes 19, e.g., on a bottom-side thereof, so as to push the reagent cassette(s) 19 onto the holder 18 or to draw it to the transport line 22. The loader/unloader 10 can have with a gripping pin for successively transporting reagent cassettes 19 by the two transport lines 22. Alternatively, each transport line 22 can have with an individual gripping pin allowing for a simultaneous transport of two reagent cassettes 19 on the two transport lines 22 in a same direction or in opposite directions. While the loader/unloader 10 is illustrated to comprise two transport lines 22, those of skill in the art will appreciate that more or less transport lines 22 can be envisaged according to the specific demands of the user. Due to the radial arrangement of the loader/unloader 10 with respect to the carousel 17, and, in light of the fact that the reagent vessels 60 contained in the incubator 21 and the reagent cassettes 19 stored by the carousel can be readily accessed from above, the loader/unloader 10 can advantageously allow the reagent cassettes 19 to be loaded to or removed from the carousel 17 even during the process of analyzing liquid samples. Furthermore, since two transport lines 22 are available, two reagent cassettes 19 can simultaneously be transported either for simultaneous loading to the carousel 17 or for loading a reagent cassette 19 to the carousel 17 and for simultaneously unloading another reagent cassette 19 from the carousel 17.

The reaction area 12 can yet further comprise an opener/closer 23 capable of opening/closing caps 26 of individual reagent cassettes 19 stored by the holders 18 of the carousel 17. With particular reference to FIGS. 7, 8A-8B and 9A-9B, the opener/closer 23 comprises a mount 61 used to fix the opener/closer 23 in the upper level 11 of the instrument 1. The opener/closer 23 further comprises a carriage 62 movably supported by the mount 61 by a translating mechanism, e.g., configured as rollers guided by linear guiding rails. Accordingly, the carriage 62 can be bidirectionally moved in an essentially horizontal plane with respect to the mount 61. Specifically, the carriage 62 can be reciprocally moved between two stop positions, i.e., a first translating position and a second translating position by translating the carriage 62 along first and second translating directions towards and away from the carousel 17.

As illustrated, in an embodiment, each reagent cassette 19 can comprise a number of, e.g., three reagent containers 24 that are fixed in serial arrangement with respect to each other. Each reagent container 24 can comprise a container body 25 for filling with reagent provided with an opening 63 closed by a cap 26 that is pivotably fixed (hinged) to the container body 25 so as to open the opening 63 by pivoting the cap 26 in a pivoting direction (opening direction) and to close the opening 63 by pivoting the cap 26 in the other (reverse) pivoting direction (closing direction). Hence, each reagent container 24 can be repeatedly opened and closed according to the scheduler explained below.

In the embodiment illustrated with respect to the figures, each reagent container 24 can comprise a cap closing mechanism (not further detailed) having a first cap closing position and a second cap closing position wherein in the first cap closing position ("hard close") the cap 26 can be more strongly fixed to the container body 25 with respect to the second cap closing position ("soft close"). For instance, in the first cap closing position, the cap 26 can be locked by a locking mechanism whereas the cap 26 may be just plugged onto the opening 63 without securing the cap 26 to the container body 25 in the second cap closing position. Accordingly, while the first cap closing position is typically used to transport or cool-store the reagent cassette 19, the second cap closing position mainly serves to prevent evaporation, spilling and contamination of fluids contained in the reagent containers 24 while in use. When using the reagent containers 24 for the first time, the caps 26 typically are in the first cap closing position and, thus, have to be initially opened. Furthermore, as illustrated, each cap 26 can have with two projecting portions 64, e.g., configured as cylindrical pins, laterally projecting from the cap 26 in an essentially horizontal plane on two opposing sides of the cap 26 for rotating the cap 26 in opening and closing directions.

Furthermore, the carriage 62 can comprise a lower, or base, portion 65 and an upper, or pivoting, portion 66 pivotably supported by the base portion 65 and being comprised of a front part 17 and a rear part 18. The pivoting portion 66 can be pivotably supported by the base portion 65 by a pivoting mechanism, e.g., configured as two horizontally arranged pairs of opposing pivot arms 67, each of which having an essentially S-like shape. Specifically, the pivoting mechanism can comprise a front pair and a rear pair wherein a lower end portion of each pivot arm 67 can be rotatably linked to the base portion 65 so that the pivot arms 16 can be pivoted with respect to the base portion 65.

The opener/closer 23 can further comprise a driven spindle drive 68 operatively coupled to the pivoting portion 66 for both translating the carriage 62 towards and away from the carousel 17, that is to say, reagent cassette 19, and pivoting the pivoting portion 66 with respect to the base portion 65. More particularly, the spindle drive 68 can comprise a frame 69 which rotatably supports an essentially horizontally aligned spindle 70. Hence, by rotating the spindle 70, a spindle nut 71 can be reciprocally translated along the spindle 70 wherein a driven shaft (not illustrated) of an electric motor 72 can be rotatably coupled to the spindle 70 so as to rotate the spindle 70 in both rotating directions. In the spindle drive 68, the spindle nut 71 can be connected to two vertically arranged pairs of opposing guiding rolls 73 so as to be entrained by the spindle nut 71 translated along the spindle 70. Furthermore, the guiding rolls 73 can be accommodated in a vertical guiding cage 74 for guidance in vertical direction. The guiding cage 74 can be connected to the pivot arms 67. Accordingly, by rotating the spindle 70, the spindle nut 71 can be translated along the spindle 70 entraining the guiding rolls 73 so as to pivot the pivot arms 67. Hence, driven by the spindle drive 68, the pivoting portion 66 can be bidirectionally pivoted with respect to the base portion 65 so as to reciprocally move the pivoting portion 66 between two stop positions, i.e., a first pivoting position and a second pivoting position along first and second pivoting directions.

The opener/closer 23 may be used to open and optionally close the caps 26 of a reagent cassette 19 positioned in front of the thereof, i.e., in the translation path of the carriage 62. For pivoting the caps 26 in opening direction and optionally closing direction, the pivoting portion 66 can have at least one pair of contact rods 75, 76 for contacting the projecting portions 64 of the caps 26 in the second translating position of the carriage 62.

Figure 8A:
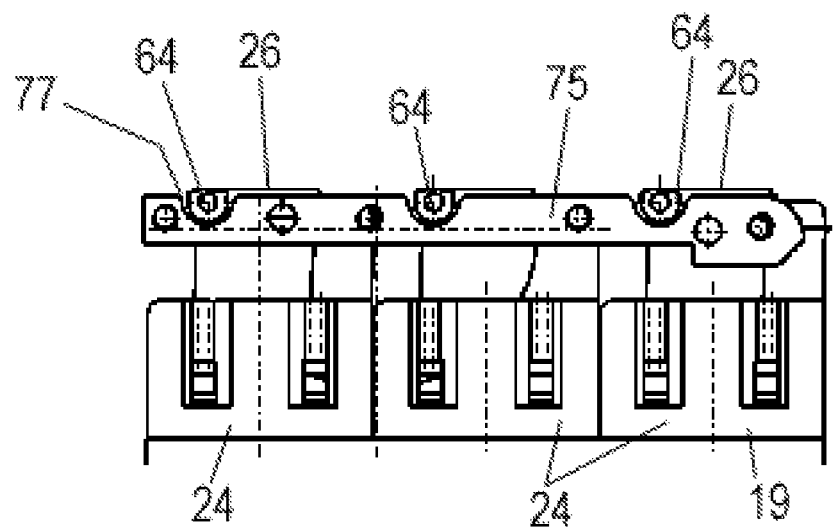
FIGS. 8A-8B are perspective views of an enlarged detail of the pivoting portion of the opener/closer of FIG. 7 according to an embodiment of the present disclosure.
Figure 8B:
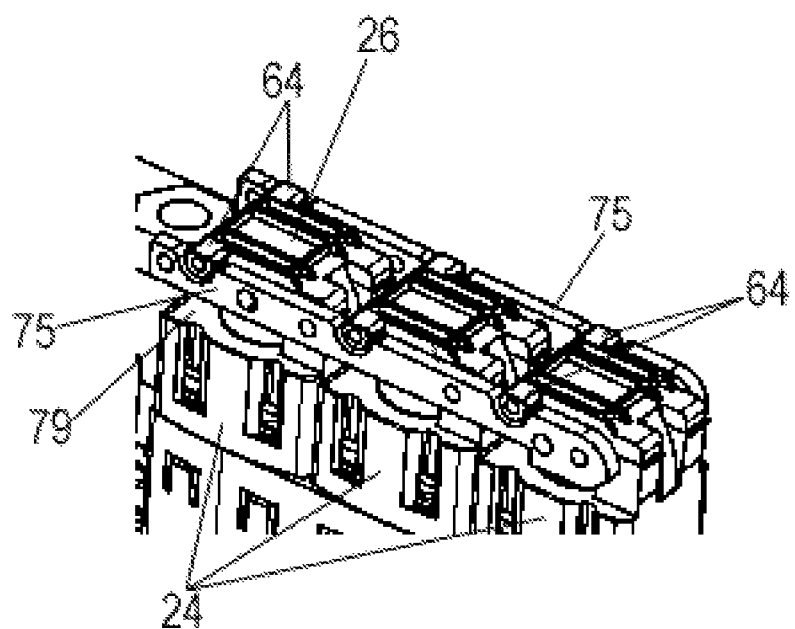

More particularly, as illustrated in FIGS. 8A and 8B, in an embodiment, the pivoting portion 66 can have a pair of two opposing lower contact rods 75 arranged in a manner to contact the projecting portions 64 or to be brought in contact with the projecting portions 64 by pivoting the pivoting portion 66 when the carriage 62 is in the second translating position with respect to the mount 61. As shown, each lower contact rod 75 can have with a number of, e.g., three semicircular recesses 77 serially arranged with respect to each other for inserting the projecting portions 64 of the caps 26. Hence, the lower contact rods 75 can be used to pivot the caps 26 in opening direction to open the reagent containers 24, and, due to inserting the projecting portions 64 in the recesses 77, can also be used to pivot the caps 26 in closing direction. Furthermore, the base portion 65 can hold the reagent cassette 19 while pivoting the caps 26 in opening or closing directions to open or close the openings 63. More particularly, the base portion 65 can have two opposing interior struts 78 which, in the second translational position of the carriage 62 can be placed in contact with upper shoulders 79 of the reagent containers 24.

Figure 9A:
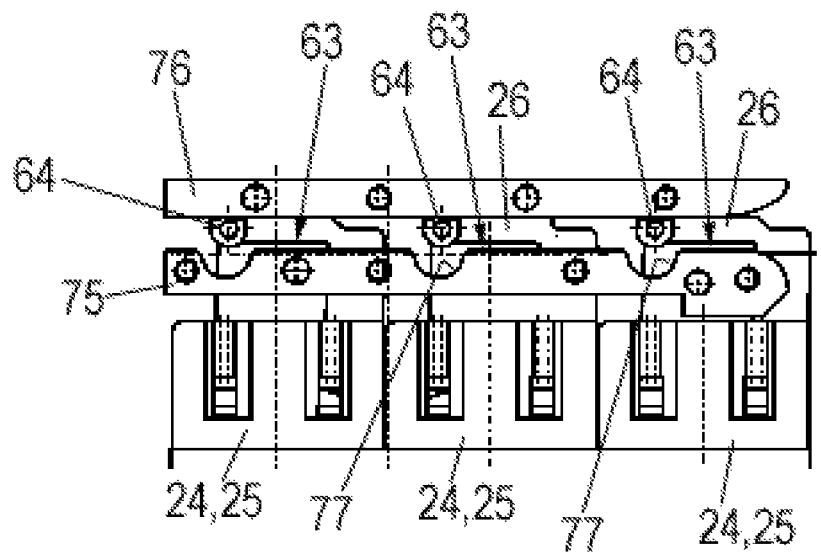
FIGS. 9A-9B are perspective views of a variant of the pivoting portion of the opener/closer of FIG. 7 according to an embodiment of the present disclosure.
Figure 9B:
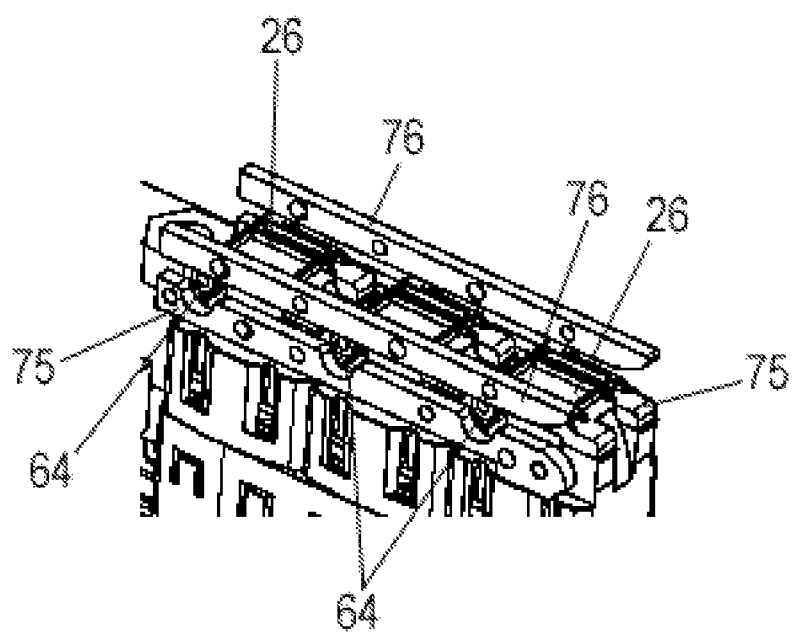

As illustrated in FIGS. 9A, 9B, in a variant thereof, the pivoting portion 66 can also be provided with one pair of two opposing lower contact rods 75 and one pair of two opposing upper contact rods 76 so that the projecting portions 64 can be positioned in-between the upper and lower contact rods 75, 76. The lower contact rods 75 can be used to pivot the caps 26 in opening direction to open the reagent containers 24. Furthermore, the upper contact rods 76 can be used to pivot the caps 26 in the reverse or closing direction to close the reagent containers 24.

Hence, each reagent container 24 can be repeatedly opened and closed according to the specific demands of the user to avoid contamination and evaporation of reagents contained therein. Since the opener/closer 23 can be arranged in a radial direction with respect to the carousel 17, individual reagent cassettes 19 stored by the holders 18 can be brought in juxtaposition to the opener/closer 23 by rotating the carousel 17. Furthermore, due to the radial arrangement of the opener/closer 23, the instrument 1 can be made highly compact in shape and the reagent cassettes 19 as well as the reaction vessels 60 contained in the incubator 21 can be readily accessed from above so as to continue sample processing even during opening/closing reagent cassettes 19. A detailed description of such opener/closer 23 and the reagent cassettes 19 associated therewith may be taken from U.S. patent application Ser. No. 13/460,867, the disclosure of which is incorporated herein by reference in its entirety.

Some reagents such as suspensions of magnetic beads need to be homogenized before use which most typically is done with a stirrer having paddles on its free end which are lowered into the reagents. Accordingly, the reaction area 12 can yet further comprise a mixer 27 comprising a re-usable vertical stirrer 28 provided with an elongated rod 56 having a paddle 57 on its lower end adapted for stifling fluids when turning the rod 56 around its longitudinal axis. The stirrer 28 can be lowered into individual reagent containers 24 stored by the holders 18 of the carousel 17. In order to avoid carry-over and cross-contamination, the stirrer 28 can be washed in-between consecutive operations. Accordingly, the instrument 1 can have an open top wash station (not illustrated) for washing the stirrer 28. More particularly, the stirrer 28 can be moved over the wash station in a position right above an opening thereof then lowered into a cavity containing wash fluid. Furthermore, a fluid jet can be generated to wash the stirrer 28. While generating such fluid jet, the paddle 57 can be turned so that all sides can be thoroughly washed. The stirrer 28 can then be moved upwards to perform the next stirring operation. As used herein, the term "wash fluid" can refer to fluids commonly used with automated clinical analyzers, e.g., aqueous solutions to which specific substances such as detergents, salts, preservatives and solubilizers have been added. Furthermore, deionized water can also be used for washing the stirrer 28. Due to the radial arrangement of the opener/closer 23 and loader/unloader 10, the stirrer 28 can have access to the carousel 17 and can readily be placed over the reagent containers 24 to be lowered into the reagents contained therein for performing a mixing operation.

While not shown in the figures, the reaction area 12 can yet further comprise an identificator, capable of identifying individual reagent cassettes 19 and/or individual reagent containers 24 located on the transport lines 22 and/or stored by the carousel 17. More particularly, each reagent cassette 19 and/or each reagent container 24 can bear a machine-readable label such as a barcode which can be automatically read by the identificator such as a barcode reader. Furthermore, each reagent cassette 19 and/or each reagent container 24 can be provided with an RFID tag (RFID=Radio-frequency identification) which can be read by the identificator. The information can be presented in machine-readable form on the label or RFID tag identifies individual reagent cassettes 19 and/or reagent containers 24 and can, for instance, code for a lot number or any other information suitable for the identification thereof. It may also contain additional information such as use-by date which may be relevant for the use of the reagents. Advantageously, the reagent cassettes 19 and/or reagent containers 24 can be identified, e.g., prior to manipulating reagents contained therein so as to improve the reliability of the sample processing.

With particular reference to FIG. 1, the reaction area 12 can yet further comprise a box-like cooling cell 29 formed by plural thick cell walls 31 made of thermally isolating material such as foamed polystyrene forming an internal space 30 thermally isolated from the surroundings.

Specifically, the cooling cell 29 can accommodate the carousel 17, the opener/closer 23 and the loader/unloader device 10. As illustrated, a front portion of the cooling cell 29 can have a first cell opening 32 opening into the internal space 30 of the cooling cell 29 and can be arranged in correspondence to the loader/unloader 10 so that reagent cassettes 19 can advantageously be placed on the transport lines 22 or removed therefrom via the first cell opening 32 essentially without compromising the cooled interior of the cooling cell 29 so as to allow for a highly efficient cooling of the cooling cell 29.

Furthermore, an upper portion of the cooling cell 29 can have three second cell openings 33 opening into the internal space 30 of the cooling cell 29 and can be arranged in correspondence to the reagent containers 24 of a reagent cassette 19 stored by the holder 18 in a dedicated rotating position allowing for the opening and optionally closing of the caps 26 by the opener/closer 23. The three second cell openings 33 can allow for the manipulation of reagents contained in the opened reagent containers 24, e.g., for mixing reagents by the mixer 27 or for pipetting reagents contained therein. While the number of second cell openings 33 typically corresponds to the number of reagent containers 24 of a reagent cassette 19, those of skill in the art will appreciate that the number and arrangement thereof may vary according to the specific demands of the user. Hence, the second cell openings 33 can advantageously allow the reagent containers 24 of a reagent cassette 19 to be accessed from above while being cooled in the cooling cell 29 so as to avoid deterioration of the reagents contained therein to improve the reliability of the test results.

Furthermore, the cooling cell 29 can have a central recess 34 thermally isolated against the cooled internal space 30 accommodating the incubator 21. Accordingly, the incubator 21 can be located outside the cooling cell 29 thermally isolated against the cooled internal space 30 so as to allow for a highly efficient cooling of the cooling cell 29. Furthermore, placing the incubator 21 in the central region 20, the instrument 1 can be made particularly compact in shape.

As above-described, the internal space 30 of the cooling cell 29 can be actively cooled by a cooling device (not illustrated) such as, but not limited to, a thermoelectric (Peltier) device utilizing the Peltier effect. As known to the skilled persons, when passing electric current through the Peltier device, depending on the direction of the current applied, the device can function as a heat sink, which can absorb heat to thereby cool the internal space 30. Accordingly, the internal space 30 of the cooling cell 29 can be cooled for cooling reagent cassettes 19 thus (cool-)stored by the holders 18 of the carousel 17 or placed on the transport lines 22 of the loader/unloader 10 while (simultaneously) heating the incubator 21 thermally insulated against the internal space 30. In one embodiment, the cooling cell 29 can, e.g., be adapted to cool-store the reagent cassettes 19 at a temperature in the range of about 6 to about 10° C. In another embodiment, the cooling cell 29 may cool-store the reagent cassettes 19 at a temperature in the range of about 6 to about 8° C.

In the instrument 1, the analytical area 13 can have at least one analyzer 35 for analyzing the reacted samples. The analyzer 35 can comprise one or more detectors or sensors for detecting reaction products such as, but not limited to, an optical detector such as a photometer, a flow-through cell coupled to an ion-selective electrode (ISE), a biosensor such as an enzymatic-electrochemical detector and an electrochemoluminescence (ECL) detector. As illustrated, in the present embodiment, the analyzer 35, e.g. can comprise an ECL-detector 54.

As illustrated in the figures, the analytical area 13 can further comprise a first reaction vessel receiving block 36 for receiving one or more reaction vessels 60 containing reacted sample. In the present embodiment, the first reaction vessel receiving block 36 can, e.g., be used to magnetically manipulate (e.g. attract) magnetically responsive particles contained in the reacted sample. More particularly, the first reaction vessel receiving block 36 can have at least one magnet (not illustrated) for generating a magnetic field, adapted for magnetically manipulating the magnetically responsive particles contained in the reaction vessel 60, in particular, for retaining the magnetically responsive particles therein. The at least one magnet can, e.g., be embodied as permanent magnet or electromagnet including a pole-shoe magnet, a switchable magnet or a toroidal magnet. Retaining the magnetically responsive particles, fluid can be removed from the reaction vessel 60, e.g., for washing out bound-free molecular detectable labels. The analytical area 13 can yet further comprise a second reaction vessel receiving block 82 for receiving one or more reaction vessels 60 from the first reaction vessel receiving block 36 for pipetting reacted sample into the analyzer 35 by a needle 55. Accordingly, in the analytical area 13, the needle 55 can be used for sucking the reacted sample from the reaction vessel 60 located in the second reaction vessel receiving block 82 into the ECL-detector 54 for detecting reaction products with respect to one or more analytes contained therein.

The ECL-detector 54 can be related to one or plural types of immunochemical methods different with respect to each other. More particularly, the optical detection of reaction products by the ECL-detector 54 can involve the production of electrochemically generated intermediates which undergo a highly exergonic reaction to produce an electronically excited state that emits light. Specifically, ECL can advantageously allow traces of micro-organisms, hormones, viruses, antibodies, amines or proteins be measured.

Figure 2:
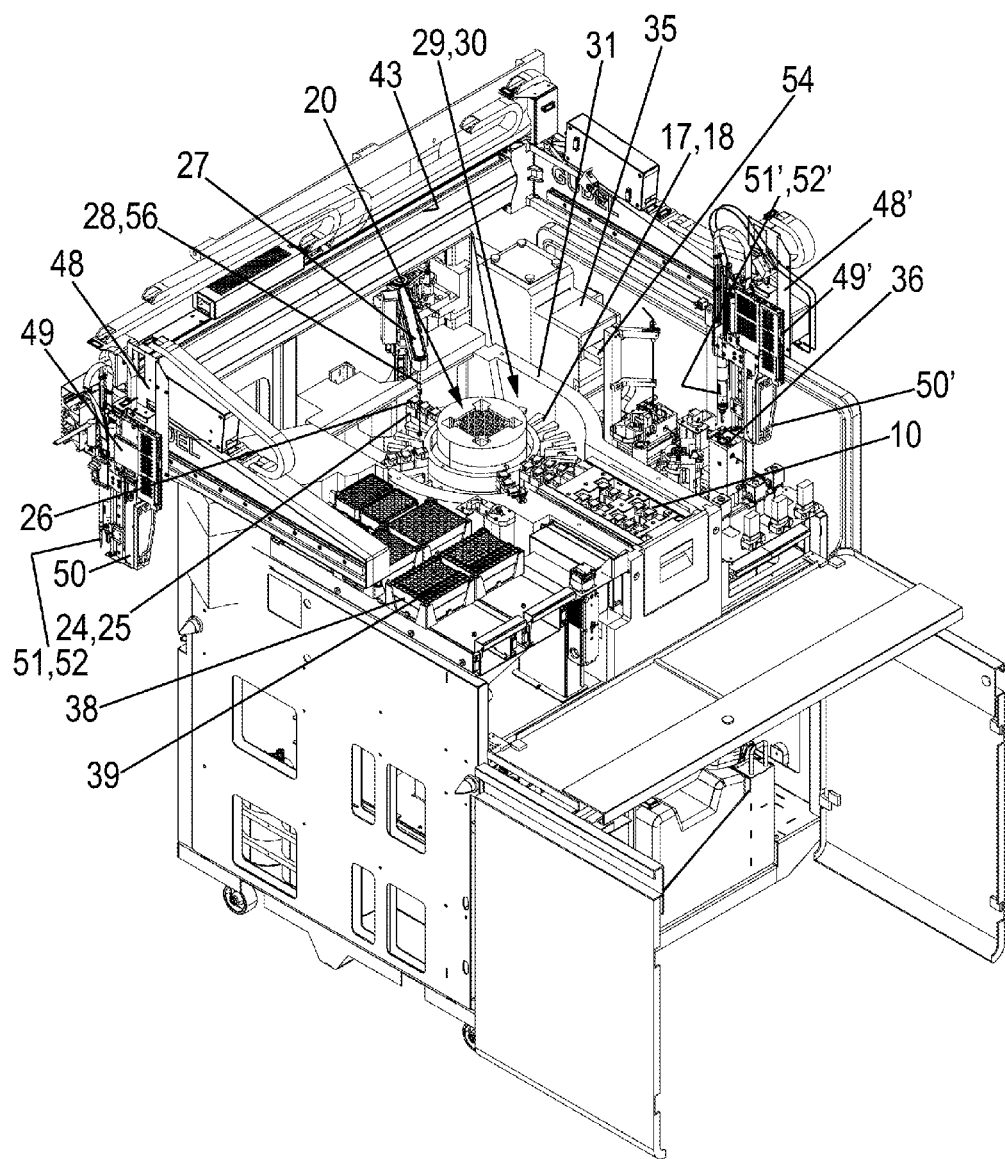
FIG. 2 is another perspective view of the first part of the exemplary instrument according to an embodiment of the present disclosure.
Figure 3:
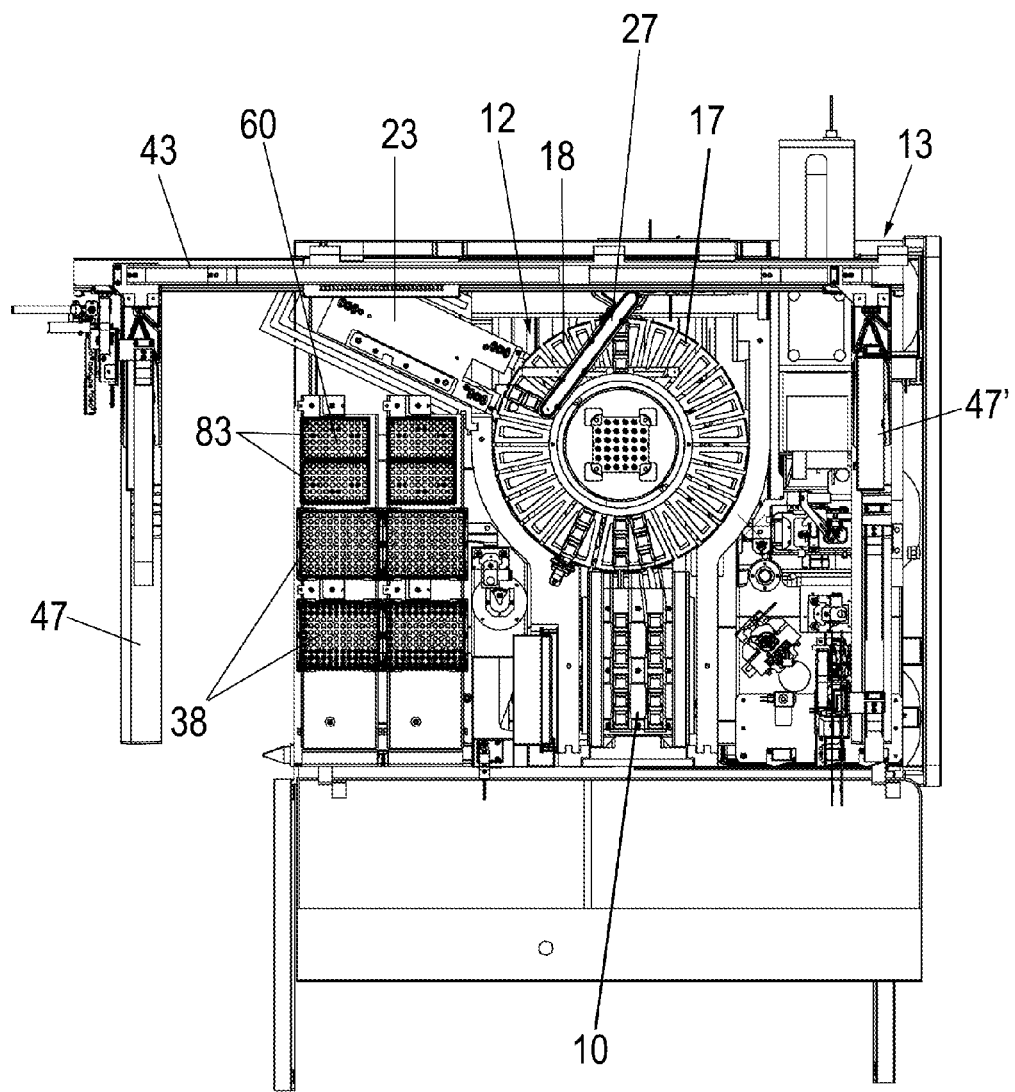
FIG. 3 is a top view of the first part of the exemplary instrument according to an embodiment of the present disclosure.
Figure 4:
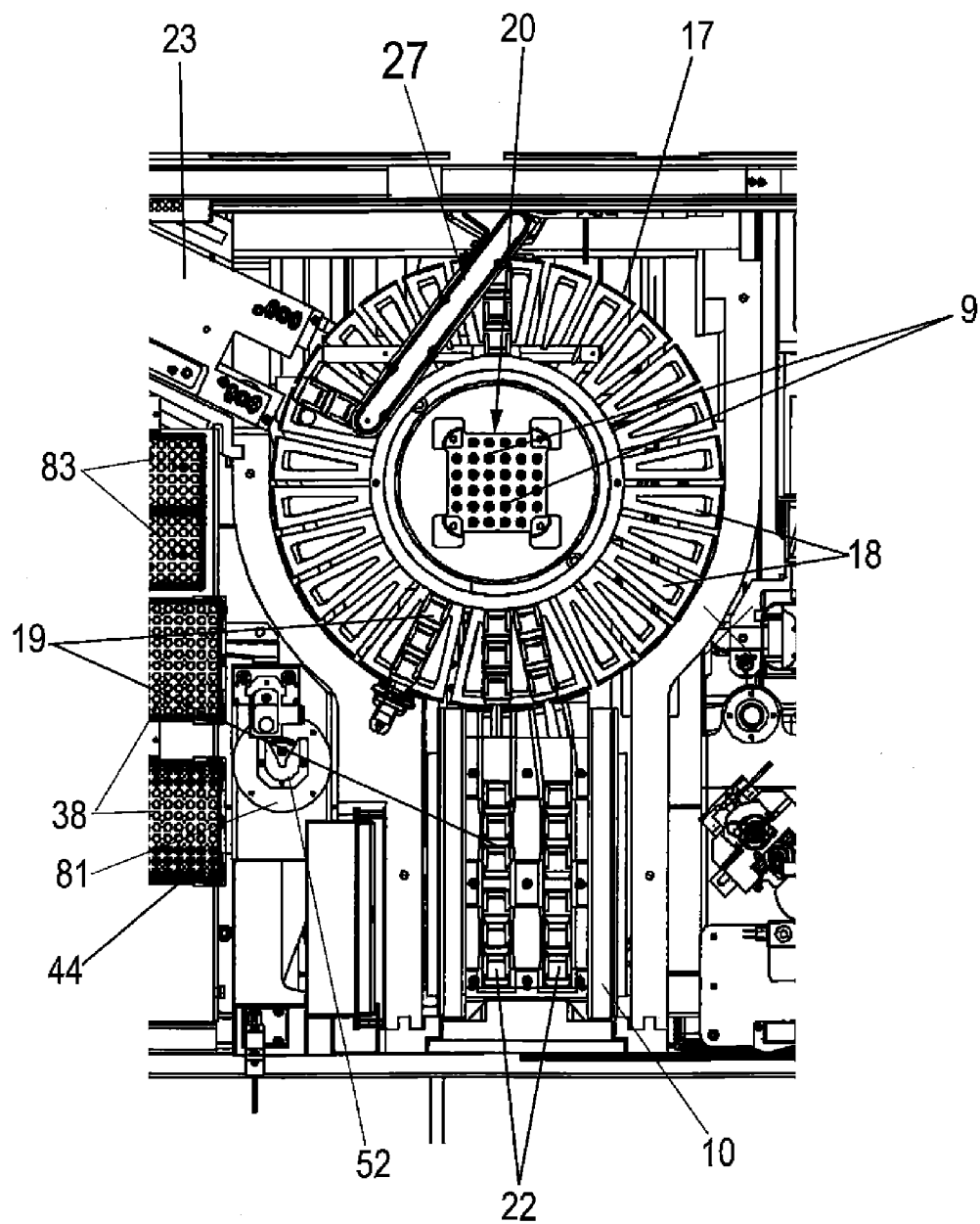
FIG. 4 depicts an enlarged detail of FIG. 3 according to an embodiment of the present disclosure.

As above-described, in the instrument 1, the sampling area 14 can comprise the disposables storing area 15 provided by the first part 2 of the instrument 1 and the sample receiving area 16 provided by the second part 3 of the instrument 1 to be put in juxtaposition to the first part 2 at the left side wall 5 thereof. Specifically, the disposables storing area 15 can comprise two slidably mounted drawers 37, each of which having plural recesses 44 for receiving tip racks 38 containing disposable pipetting tips 39 for pipetting fluids and reaction vessel racks 83 containing disposable reaction vessels 60. The drawers 37 can be drawn out of the instrument 1 at the front-side 45 thereof to be charged with new (filled) tip racks 38 and reaction vessel racks 83, respectively, or uncharged with used (empty) tip racks 38 and reaction vessel racks 83, respectively. While two drawers 37 respectively containing four tip racks 38 and four reaction vessel racks 83 are shown in FIGS. 1 and 2 for the purpose of illustration only, it is to be understood that the instrument 1 can contain any other number and arrangement of drawers 37, tip racks 38 and reaction vessel racks 83 that would be compatible with the automated instrument 1 for analyzing liquid samples. By using disposable pipetting tips 39 and disposable reaction vessels 60 (cross-)contamination of liquid samples and reagents can advantageously be avoided.

Figure 6:
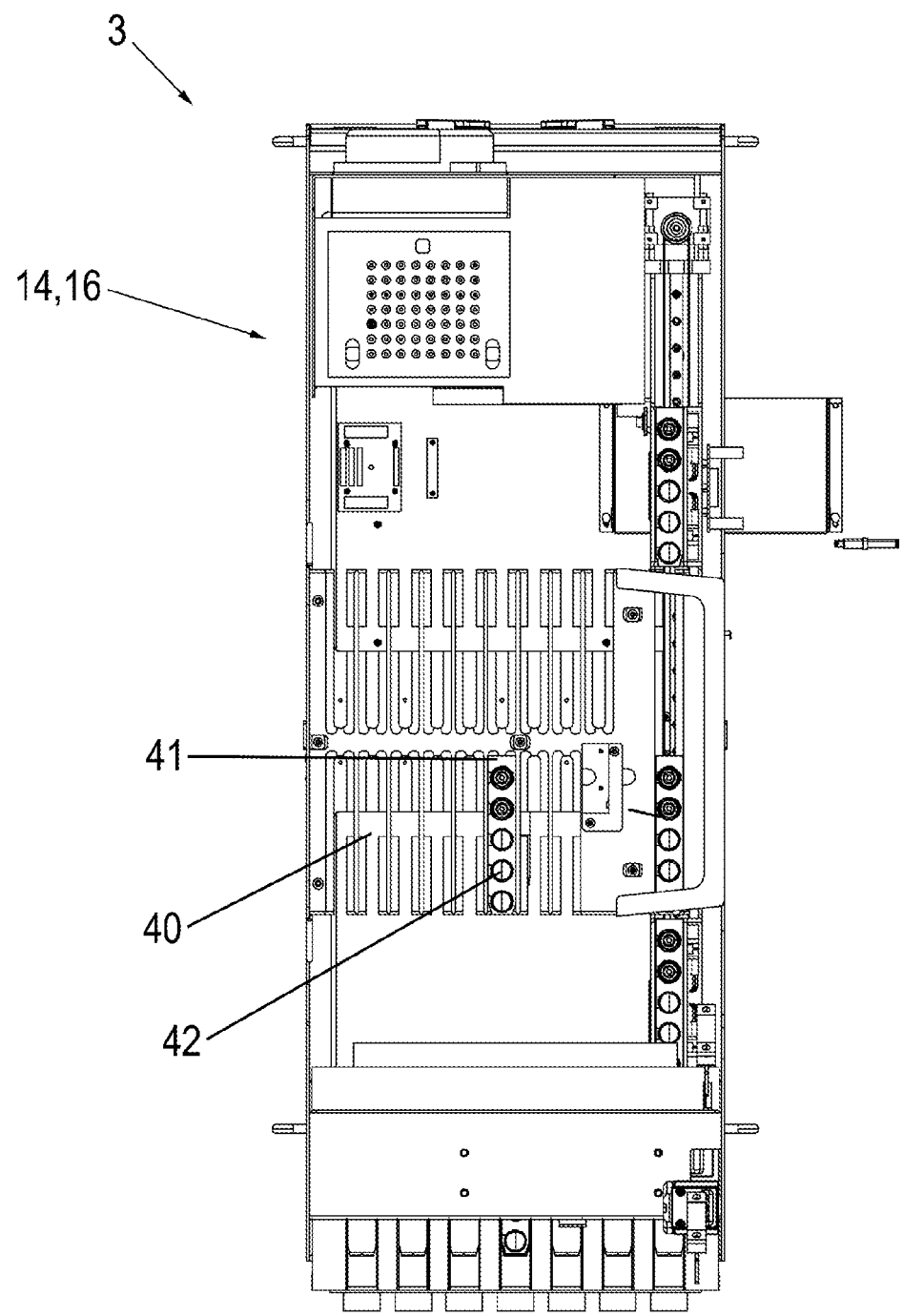
FIG. 6 is a top view of the second part of the exemplary instrument according to an embodiment of the present disclosure.
Figure 7:
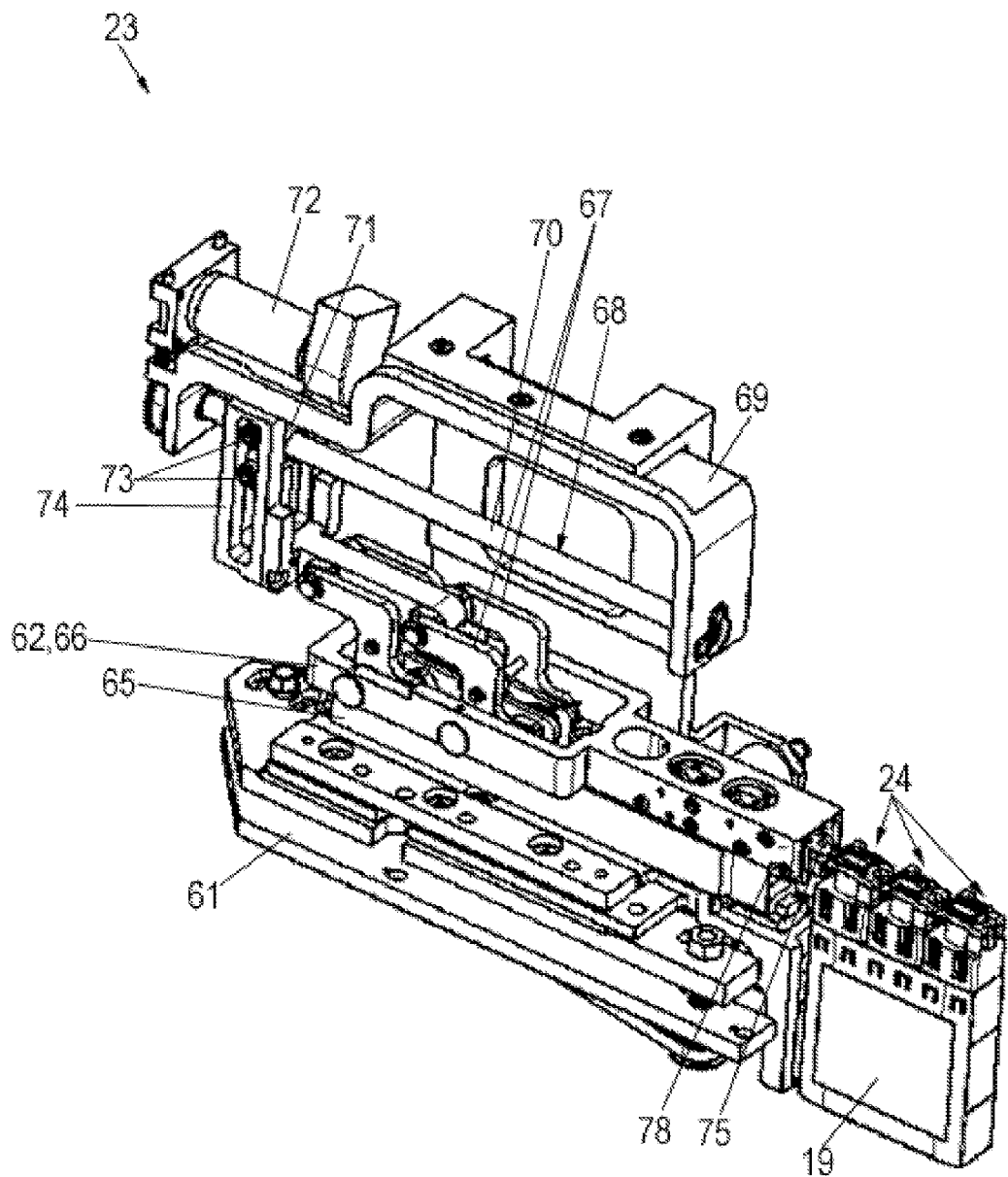
FIG. 7 is a perspective view of an opener/closer of the exemplary instrument according to an embodiment of the present disclosure.

Furthermore, as illustrated in FIGS. 5 and 6, the sample receiving area 16 can have a plurality of slots 40, each of which being adapted for receiving a sample rack 41 for carrying a number of open-top sample tubes 42 serially arranged with respect to each other for receiving samples to be analyzed. While five sample tubes 42 are shown to be contained in a sample rack 41 for the purpose of illustration only, each sample rack 41 can have any other number and arrangement of sample tubes 42 that would be compatible with the automated instrument 1 for analyzing liquid samples.

The instrument 1 can yet further comprise two separate two-rail translation systems 46, 46', i.e., a first translation system 46 and a second translation system 46', each of which comprising two rails comprised of a common back rail 43 and individual transfer head rails 47, 47', i.e., a first transfer head rail 47 and a second transfer head rail 47', arranged in orthogonal relationship with respect to each other. The two two-rail translation systems 46, 46' are similar in construction. More particularly, each two-rail translation system 46, 46' can comprise the (common) back rail 43 extending in one direction (x) slidably engaged with the transfer head rail 47, 47' extending in the orthogonal direction (y) thereof in a horizontal plane. Accordingly, each transfer head rail 47, 47' can be translatably moved along the back rail 43 in the direction (x). Furthermore, the first and second transfer head rails 47, 47' respectively can have a transfer head 48, 48', i.e., the first transfer head rail 47 can have a first transfer head 48 and the second transfer head rail 48' can have a second transfer head 48' slidably mounted thereto so that the transfer heads 48, 48' can be translatably moved along the transfer head rail 47, 47', respectively, in the orthogonal direction (y). Accordingly, the transfer heads 48, 48' can be moved in two directions of travel over a horizontal plane. Furthermore, each transfer head 48, 48' can have a mounting block 49, 49', i.e., the first transfer head 48 can have a first mounting block 49 and the second transfer head 48' can have a second mounting block 49', slidably mounted to the transfer head 48, 48', respectively, so that the mounting blocks 49, 49' can be translatably moved in vertical direction (z). Accordingly, the mounting blocks 49, 49' can be moved in three orthogonal directions of travel. The translation of the mounting blocks 49, 49' can, e.g., be based on motor-driven spindle-drives not further elucidated herein.

Specifically, the first and second mounting blocks 49, 49' respectively can have a gripper 50, 50' for gripping a sample tube 42. Furthermore, the first mounting block 49 (the left as seen from the front-side 45) can have a first pipettor 51 for pipetting fluids configured for use with disposable pipetting tips 39 stored in the disposable storing area 15. Due to being mounted to a same mounting block 49 the first gripper 50 can be transferred together with the first pipettor 51.

Furthermore, the second mounting block 49' (the right as seen from the front-side 45) can have a second pipettor 51' for pipetting fluids embodied as re-usable metallic needle. Due to being mounted to a same mounting block 49', the second gripper 50' can be transferred together with the second pipettor 51'. For washing the metallic needle, the wash station described in connection with the stirrer 28 can be used. Alternatively, as illustrated, the instrument 1 can also be provided with a separate needle wash station 80 for washing the metallic needle 55 which may be of similar construction with respect to the wash station of the stirrer 28.

In the instrument 1, the first two-rail translation system 46 arranged on the left side thereof (as seen from the front-side 45) can be used for gripping reaction vessels 60 and pipetting liquids only in the reaction area 12 and the sampling area 14 but not in the analytical area 13. More particularly, the first translation system 46 can, e.g., be used to transfer reaction vessels 60 from the sampling area 14 to the incubator 21, to pipette samples from the sample receiving area 16 into the reaction vessel 60 contained in the incubator 21 and to pipette reagent(s) from the reagent cassettes 19 stored by the carousel 17 to the reaction vessel 60 contained in the incubator 21. Furthermore, the second two-rail translation system 46' arranged on the right side of the instrument 1 (as seen from the front-side 45) can be used for gripping reaction vessels 60 and pipetting liquids only in the reaction area 12 and the analytical area 13 but not in the sampling area 14. More particularly, the second translation system 46' can, e.g., be used to transfer reaction vessels 60 from the incubator 21 to the first and second reaction vessel receiving blocks 36, 82 of the analytical area 13, to remove reaction vessels 60 from the second reaction vessel receiving block 83 to transfer the reaction vessels 60 into a waste container (not illustrated) and to pipette fluids with respect to reaction vessels 60 contained in first reaction vessel receiving block 36.

The two two-rail translation systems 46, 46' having only one (common) backrail 43 can advantageously allow for a highly compact construction of the instrument 1 in which the first and second transfer head rails 47, 47' can be made comparably short. This can especially apply to the specific arrangement of the reaction area 12 arranged in-between the sampling area 14 and the analytical area 13. Furthermore, since the loader/unloader 10 and the opener/closer 23 can be radially arranged with respect to the carousel 17, the first and second transfer head rails 47, 47'can be readily moved to have (alternatively) free access to the incubator 21 and the carousel 17, respectively.

The instrument 1 can further comprise a controller 53 (not further illustrated) for controlling the operation of the instrument 1 for analyzing liquid samples. The controller 53 may, e.g., be embodied as programmable logic controller running a machine-readable program provided with instructions to perform operations in accordance with a predetermined process operation plan for processing samples by mixing samples with one or more reagents so as to obtain sample/reagent mixtures, incubating the sample/reagent mixtures to obtain reacted samples and analyzing the reacted samples by the analyzer 35. The controller 53 can be electrically connected to the various instrument components requiring control so as to transmit control signals and check the result of such control by response signals. Particularly, the controller 53 can comprise a hardware and/or software component related to as scheduler configured to generate and assign time slots for operating devices resources as detailed below of the instrument 1. A second device resource can comprise the first gripper 50 and the first pipettor 51. A third device resource can comprise the second gripper 50' and the second pipettor 51'. A first device resource can comprise devices contained in the analytical area 13 comprising the analyzer 35 and the pipettor thereof comprising the needle 55. More particularly, the scheduler of the controller 55 can be set up to successively operate the various functional devices to process a sample. Furthermore, the scheduler is configured to operate the first to third device resources at least temporarily (partly) in parallel to process two or more liquid samples. Furthermore, the scheduler can be set up in a manner that the devices connected to the first mounting block 49, i.e., the first gripper 50 and the first pipettor 51, can have exclusive access to the reaction area 12 and the sampling area 14 (and not to the analytical area 13), and, that the devices connected to the second mounting block 49', i.e., the second gripper 50' and the second pipettor 51', can have exclusive access to the reaction area 12 and the analytical area 13 (and not to the sampling area 14).

As above-detailed, in the instrument 1, the sampling area 14 can be arranged on one side of the reaction area 12 and the analytical area 13 can be arranged on the other side thereof. Combined with the two two-rail translation systems 46, 46', reaction vessels 60 and liquids contained therein can simultaneously be processed. Hence, e.g., a new reaction vessel 60 can be transferred from the sampling area 14 to the incubator 21 during processing of a reacted sample in the analytical area 13. Furthermore, the carousel 17 can, e.g. continuously, be loaded with or unloaded from reagent cassettes 19 while samples are processed. Furthermore, reagent cassettes 19 can be opened or closed by the opener/closer 23 without hindering the operation of the two two-rail translation systems 46, 46' and the functional devices combined therewith. Accordingly, liquid samples can very quickly be processed. Furthermore, a major advantage can be given by the fact that sample/reagent mixtures can be incubated in thermal insulation to the cool-stored reagent cassettes 19 on the carousel 17 so that undesired condensation of water can largely be prevented.

Figure 10:
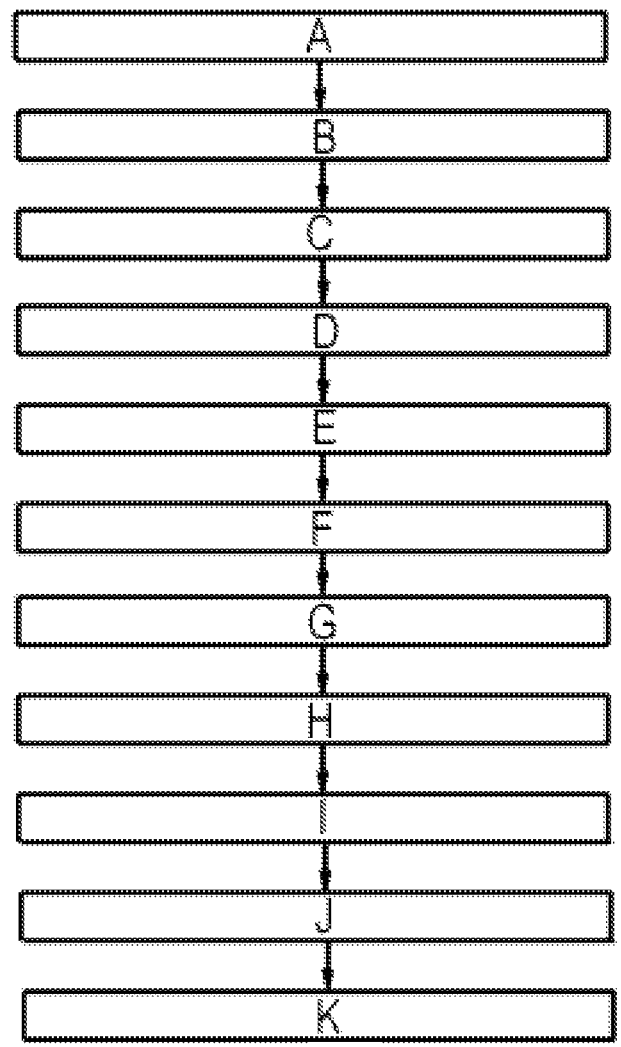
FIG. 10 is a flow chart illustrating an exemplary embodiment of a process for analyzing liquid samples according to an embodiment of the present disclosure.

Now referring to FIG. 10, which is a schematic flow diagram, an exemplary embodiment of the process for analyzing a liquid sample under control of the controller 53 is explained. The analysis of the sample can be based on combining the sample with one or more reagents, one of which can contain magnetically responsive particles embodied as magnetic beads made of magnetically responsive material provided with immobilized reactants such as antibodies adapted to specifically bind to at least one analyte contained in the sample.

The process starts (step A) with providing an instrument 1 as above-detailed provided with tip racks 38 containing pipetting tips 39 and empty reaction vessels 60 in the disposables storing area 15, sample racks 41 containing sample tubes 42 with liquid samples in the sample receiving area 16 and reagent cassettes 19 can be loaded onto the carousel 17 which can be actively cooled within the cooling cell 29.

In the next step (step B), an empty reaction vessel 60 can be transferred from the reaction vessel rack 83 of the disposables storing area 15 to a receptacle 9 of the incubator 21 using the first gripper 50 of the left (first) translation system 46.

In the next step (step C), the carousel 17 can be rotated to selectively move a reagent cassette 19 in an opening/pipetting position in juxtaposition to the opener/closer 23, followed by opening the reagent containers 24 thereof by the opener/closer 23.

In the next step (step D), the first pipettor 51 of the left (first) translation system 46 can be lowered to an unused pipetting tip 39 contained in a tip rack 38 of the disposables storing area 15 so that the pipetting tip 39 can be fixed thereto, followed by pipetting reagent from one or more reagent containers 24 of the reagent cassette 19 to the reaction vessel 60 in the incubator 21. For aspirating reagent into the pipetting tip 39, the first pipettor 51 can be lowered and inserted into the desired reagent container 24 through one of the second cell openings 33. In an embodiment, prior to pipetting, reagent (e.g. reagent containing magnetic beads) can be mixed by the stirrer 28 by lowering the stirrer 28, inserting the paddle 57 into the reagent container 24 through the second cell opening 33 and rotating the rod 56 along its longitudinal axis so as to mix the reagent by the paddle 57.

In the next step (step E), the used pipetting tip 39 of the first pipettor 51 of the left (first) translation system 46 can be removed by lowering the first pipettor 51 into a tip waste container 81, and, by contacting a projection 83 thereof while moving the first pipettor 51 upwards, striping the pipetting tip 39 off the first pipettor 51. Hence, the used pipetting tip 39 can be discharged in the tip waste container 81. Then, the first pipettor 51 of the left (first) translation system 46 can be lowered to an unused pipetting tip 39 contained in a tip rack 38 of the disposables storing area 15 so that the pipetting tip 39 can be fixed thereto.

In the next step (step F), a liquid sample can be pipetted from the sample receiving area 16 to the reaction vessel 60 contained in the incubator 21 using the first pipettor 51 so as to obtain a sample-reagent mixture.

The above-detailed step E, followed by step D, can be repeated once or several times in case more than one reagent is to be pipetted to the reaction vessel 60 received in the incubator 21.

In the next step (step G), the sample/reagent(s) mixture can be incubated for a predetermined time-interval so as to obtain a reacted sample. While incubating the sample/reagent(s) mixture contained in the reaction vessel 60 located in the incubator 21, the reagent cassettes 19 contained in the cooling cell 29 which are stored by the carousel 17 and placed on the transport lines 22 of the loader/unloader 10, respectively, can be actively cooled in thermal insulation with respect to the incubator 21.

In the next step (step H), after incubation, the reaction vessel 60 containing the reacted sample can be transferred from the incubator 21 to the first reaction vessel receiving block 36 of the analytical area 13 using the second gripper 50' of the right (second) translation system 46'.

In the next step (step I), the magnetic beads contained in the reaction vessel 60 can be drawn to the inner side thereof so as to allow for withdrawal of fluid, e.g., for washing out bound-free molecular detectable labels using the second pipettor 51' embodied as re-usable metallic needle of the right (second) translation system 46'. Furthermore, fluid(s) can be filled into the reaction vessel 60. Prior to or after pipetting fluid(s) with respect to the reaction vessel 60 located in the reaction vessel receiving block 36, the second pipettor 51' can be washed to avoid carry-over.

In the next step (step J), the reaction vessel 60 containing the reacted sample can be transferred to the second reaction vessel receiving block 82 by the second gripper 50'.

In the next step (step K), the processed reacted sample can be transferred from the reaction vessel 60 located in the second reaction vessel receiving block 82 to the ECL-detector 54 for analysis with respect to one or more analytes contained therein using the metallic needle 55. Then, the reaction vessel 60 can be removed from the second reaction vessel receiving block 82 using the second gripper 50' of the right (second) translation system 46' and transferred to a waste container (not illustrated).

In the above-detailed process, the two translation systems 46, 46' can be moved simultaneously and, furthermore, the first gripper 50 and first pipettor 51 of the left (first) translation system 46 can be operated simultaneously with the second gripper 50' and second pipettor 51' of the right (second) translation system 46' so as to save time in processing liquid samples. More particularly, while manipulating the reaction vessel 60 located in the first or second reaction vessel receiving blocks 36, 82 and/or manipulating reacted sample contained therein, another reaction vessel 60 and/or sample and/or reagent(s) can be transferred to the incubator 21. Furthermore, the reagent containers 24 can be opened for pipetting and/or mixing reagent(s) contained therein, and, can be closed in the remaining time to avoid evaporation of reagents and contamination by small particles (particulate matter or dust) contained in the air. Specifically, the reagent containers 24 can be opened or closed while the two translation systems 46, 46' and the grippers 50, 50' and pipettors 51, 51' combined therewith are working to advantageously save time in analyzing the samples.

The above-detailed process may, e.g., comprise a further step of closing the caps 26 of the reagent containers 24 stored in the carousel 17 after pipetting reagent(s). It may comprise a yet further step of identifying reagent containers 24 stored by the carousel 17.

In an embodiment, in the above-described process, the various steps (A-K) can be performed successively (sequentially). In another embodiment, at least two steps thereof can be at least partially performed in parallel. In an embodiment, in the above-described process, the steps (A-K) can be performed in the described alphabetical order but a different order may also be considered.

From the former detailed description of exemplary embodiments of the invention, it can become apparent that samples can be readily processed and analyzed by the instrument 1 which can be made very small in height and compact in shape. Due to the central arrangement of the reaction area 12 in-between the sampling area 14 and the analytical area 13 combined with the loader/unloader 10 and opener/closer 23, both of which are radially arranged with respect to the carousel 17, the instrument 1 can be made highly compact to have a comparably small footprint allowing for a quick and cost-efficient analysis of the samples in which the first and (alternatively) second transfer head rails 47, 47' can be readily moved over the incubator 21 and the carousel 17. Accordingly, the carousel 17 and the incubator 21 can be readily accessed from above so that the opener/closer 23 and/or the loader/unloader 10 can be operated while performing other processing operations using the first and second pipettors 51, 51' and grippers 50, 50'. Furthermore, the two translation systems 46, 46', each including a pipettor 51, 51' and a gripper 50, 50', can be used to perform various simultaneous operations so as to save time in processing liquid samples. Specifically, loading/unloading of reagent cassettes 19 to/from the carousel 17, transfer of reaction vessels 60 to or alternatively from the incubator 21, pipetting of samples and/or reagents, incubation of sample/reagent(s) mixtures, opening and closing of caps 26 prior to or after performing a pipetting operation can simultaneously be performed. Furthermore, due to the compact shape of the instrument 1, the two translation systems 46, 46' can be operated to have a minimum drive range. The scheduler of the controller 53 can be configured to sequentially (successively) operate the various device resources for processing a sample wherein at least two device resources can at least temporarily be operated in parallel for processing two or more samples by generating and assigning time slots for operating the devices concerned. Hence, liquid samples can be processed in a highly time- and cost-effective manner.

It is noted that terms like "commonly," "generally", "particularly" and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "essentially" is utilized herein to represent the inherent degree of uncertainty that may be attributed to any quantitative comparison, value, measurement, or other representation. The term "essentially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An automated instrument for processing liquid samples contained within reaction vessels comprising:
   an upper level bordered by a first side wall and a second side wall, the automated instrument further comprising,
   a sampling unit on the upper level of the automated instrument located near the first side wall, the sampling unit receives the liquid samples and the reaction vessels;
   a first device resource comprising at least one analytical device for analyzing the liquid samples, wherein the first device resource is located in an analytical unit, the analytical unit is located by the second side wall of the upper level of the automated instrument;
   a ring-shaped reagent carousel comprising a plurality of holders for storing reagent containers containing reagents, wherein the reagent carousel is located in a reaction unit, the reaction unit is arranged between the analytical unit and the sampling unit on the upper level of the automated instrument and wherein the plurality of holders at least partly surrounds a non-rotatable central region of the ring-shaped reagent carousel;
   an incubator configured for receiving one or more of the reaction vessels for incubating the liquid samples contained therein, wherein the incubator is located within the non-rotatable central region of the ring-shaped reagent carousel and wherein the incubator is stationary with respect to the automated instrument so that the reagent carousel is circumferentially movable with respect to the incubator;
   a first rail translation device resource mounted on the first side wall of the automated instrument comprising first functional devices comprising a first gripper for gripping the reaction vessels and a first pipettor for pipetting liquids, wherein the first functional devices have access to the sampling unit and the reaction unit such as to transfer reaction vessels from the sampling unit to the incubator and to pipette liquid samples and/or reagents into the reaction vessels on the sampling unit;
   a second rail translation device resource mounted on the second side wall of the automated instrument comprising second functional devices comprising a gripper for gripping the reaction vessels and a second pipettor for pipetting liquids, wherein the second functional devices have access to the reaction unit and the analytical unit such as to transfer reaction vessels from the incubator to the analytical unit and to dispense and/or withdraw one or more liquids to/from the reaction vessels transferred to the analytical unit;
   a first transfer head rail movable in a first direction and comprising at least one first transfer head movable in a second direction perpendicular to the first direction for mounting the first functional devices of the first rail translation device resource;
   a second transfer head rail movable in the first direction and comprising at least one second transfer head movable in the second direction for mounting the second functional devices of the second rail translation device resource; and
   a controller located within the automated instrument and electrically connected to the first device resource, first rail translation device resource and second rail translation device resource device resource to transmit control signals and check the result of such control signals by response signals in order to process the liquid samples, wherein at least two of the first device resource, first rail translation device resource and second rail translation device resource device resource are at least temporarily operated in parallel for processing two or more liquid samples.

2. The instrument according to claim 1, further comprising a cooling cell to accommodate the ring-shaped reagent carousel within the cooling cell for actively cooling the reagent containers stored by the plurality of holders, wherein the cooling cell has a thermally isolated central recess to accommodate the incubator.

3. The instrument according to claim 2, wherein a loader/unloader device is at least partially contained in the cooling cell.

4. The instrument according to claim 1, wherein the reagent carousel is operatively coupled to one or more of the following devices selected from:
   a loader/unloader, capable of loading and unloading the reagent containers to and from the holders;
   an opener/closer, capable of opening and closing caps of the reagent containers stored by the conveyor;
   a mixer, capable of mixing reagents contained in the reagent containers stored by the conveyor;
   an identificator, capable of identifying the reagent containers stored by the conveyor.

5. The instrument according to claim 1, wherein disposable pipetting tips for the first pipettor are stored within the sampling unit.

6. The instrument according to claim 2, wherein an opener/closer device is at least partially contained in the cooling cell.

* * * * *